United States Patent
Takahashi et al.

(10) Patent No.: US 11,446,214 B2
(45) Date of Patent: *Sep. 20, 2022

(54) CURABLE DENTAL COMPOSITE

(71) Applicant: GC CORPORATION, Shizuoka (JP)

(72) Inventors: Akio Takahashi, Kasugai (JP);
Takayuki Murata, Tokyo (JP);
Takumasa Kimura, Tokyo (JP)

(73) Assignee: GC CORPORATION, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/762,018

(22) PCT Filed: May 10, 2019

(86) PCT No.: PCT/JP2019/018680
§ 371 (c)(1),
(2) Date: May 6, 2020

(87) PCT Pub. No.: WO2020/031444
PCT Pub. Date: Feb. 13, 2020

(65) Prior Publication Data
US 2020/0352830 A1 Nov. 12, 2020

(30) Foreign Application Priority Data

Aug. 8, 2018 (JP) .............................. JP2018-149484

(51) Int. Cl.
*A61K 6/896* (2020.01)
*A61C 5/00* (2017.01)

(52) U.S. Cl.
CPC ................ *A61K 6/896* (2020.01); *A61C 5/00* (2013.01)

(58) Field of Classification Search
CPC .................................................... A61K 6/896
See application file for complete search history.

(56) References Cited

U.S. PATENT DOCUMENTS

| | | | |
|---|---|---|---|
| 3,442,851 A | 5/1969 | McManimie et al. | |
| 5,192,815 A | 3/1993 | Okada et al. | |
| 5,354,785 A | 10/1994 | Rheinberger et al. | |
| 6,306,927 B1 | 10/2001 | Blackwell et al. | |
| 6,500,004 B2 | 12/2002 | Jensen et al. | |
| 6,593,395 B2 | 7/2003 | Angeletakis et al. | |
| 6,812,266 B2 | 11/2004 | Klee et al. | |
| 6,890,968 B2 | 5/2005 | Angeletakis et al. | |
| 6,899,948 B2 | 5/2005 | Zhang et al. | |
| 7,001,932 B2 | 2/2006 | Blackwell et al. | |
| 7,275,932 B2 | 10/2007 | Jin et al. | |
| 7,393,882 B2 | 7/2008 | Wu et al. | |
| 7,780,449 B2 | 8/2010 | Fischer | |
| 7,828,550 B2 | 11/2010 | Wagner et al. | |
| 7,951,851 B2 | 5/2011 | Kuboe et al. | |
| 8,278,368 B2 | 10/2012 | Rusin et al. | |
| 8,436,078 B2 | 5/2013 | Okubayashi et al. | |
| 8,440,739 B2 | 5/2013 | Okubayashi et al. | |
| 8,455,564 B2 | 6/2013 | Kuboe et al. | |
| 8,552,087 B2 | 10/2013 | Zappini | |
| 8,710,114 B2 | 4/2014 | Rusin et al. | |
| 8,790,707 B2 | 7/2014 | Rusin et al. | |
| 8,957,126 B2 | 2/2015 | Rusin et al. | |
| 9,109,072 B2 | 8/2015 | Takahashi et al. | |
| 9,119,774 B2 | 9/2015 | Gross et al. | |
| 9,724,275 B2 | 8/2017 | Schuhmacher et al. | |
| 10,137,061 B2 | 11/2018 | Rusin et al. | |
| 10,441,512 B2 | 10/2019 | Tanaka et al. | |
| 2003/0162863 A1 | 8/2003 | Satoh et al. | |
| 2010/0105802 A1 | 4/2010 | Kuboe et al. | |
| 2013/0172441 A1 | 7/2013 | Takahata et al. | |
| 2014/0378571 A1 | 12/2014 | Takahashi et al. | |
| 2015/0272833 A1 | 10/2015 | Toriyabe et al. | |
| 2015/0320646 A1 | 11/2015 | Kameya et al. | |
| 2018/0049953 A1 | 2/2018 | Tanaka et al. | |
| 2019/0380918 A1 | 12/2019 | Murata et al. | |

FOREIGN PATENT DOCUMENTS

| | | |
|---|---|---|
| CN | 103118626 A | 5/2013 |
| CN | 104797232 A | 7/2015 |
| EP | 3 381 435 A2 | 10/2018 |
| EP | 3 381 435 A3 | 10/2018 |
| EP | 3 586 814 A1 | 1/2020 |
| ER | 3 272 325 A1 | 1/2018 |
| JP | 02-134307 A | 5/1990 |
| JP | 2017-014111 A | 1/2017 |
| WO | 02/05752 A1 | 1/2002 |
| WO | 2008/093596 A1 | 8/2008 |
| WO | 2014/050634 A1 | 4/2014 |
| WO | 2014/083842 A1 | 6/2014 |
| WO | 2016/152659 A1 | 9/2016 |

OTHER PUBLICATIONS

International Search Report for PCT/JP2019/018680 dated Jun. 18, 2019 [PCT/ISA/210].
"A basic guide to particle characterization", 2015, XP055780752, Retrieved from: URL: <https://www.cif.iastate.edu/sites/default/files/uploads/Other_Inst/Particle%20Size/Particle%20Characterization%20Guide.pdf> (24 pages total).
International Search Report dated Jan. 16, 2018 from the International Searching Authority in application No. PCT/JP2017/043871.

(Continued)

*Primary Examiner* — Benjamin J Packard

(74) *Attorney, Agent, or Firm* — Sughrue Mion, PLLC

(57) ABSTRACT

A polymerizable monomer, a filler (A), and a filler (B) are contained, the filler (A) includes an inorganic particle and a compound covering the inorganic particle, the filler (B) includes another inorganic particle and another compound covering the other inorganic particle, and the average particle size of the filler (B) is 20% to 550% of the average particle size of the filler (A).

2 Claims, No Drawings

(56) References Cited

OTHER PUBLICATIONS

Non-Final Office Action dated Oct. 1, 2020 issued by USPTO in U.S. Appl. No. 16/488,673.
Notice of Allowance dated Oct. 28, 2020 issued by the USPTO in U.S. Appl. No. 16/488,673.
U.S. Appl. No. 16/488,673, filed Aug. 26, 2019 (Murata).

CURABLE DENTAL COMPOSITE

CROSS REFERENCE TO RELATED APPLICATIONS

This application is a National Stage of International Application No. PCT/JP2019/018680, filed on May 10, 2019, which claims priority from Japanese Patent Application No. 2018-149484, filed on Aug. 8, 2018.

TECHNICAL FIELD

The present disclosure relates to a curable dental composite.

BACKGROUND ART

A flowable composite resin is one of curable dental composites, and generally contains a polymerizable monomer and a filler. A flowable composite resin is widely used as a material for filling and restoring the regions of defects and caries of the teeth.

In addition to such basic dental properties, functions such as polishability, abrasion resistance, formability, handleability, and flexural strength are demanded of a flowable composite resin.

Flowability is also demanded of a flowable composite resin for filling affected regions with a flowable composite resin in dental treatment. Various degrees of flowability are demanded according to cases etc. In clinical settings, a plurality of flowable composite resins each having different degrees of flowability (sagging) are demanded. Various flowable composite resins having wide-ranging degrees of flowability are required.

Patent Literature 1 discloses a flowable composite resin whose polishability, abrasion resistance, formability and handleability, and flexural strength may be all met at the same time. This flowable composite resin contains a polymerizable monomer and two types of inorganic particles. Each of the inorganic particle is surface-treated in a predetermined manner and has a predetermined particle size.

CITATION LIST

Patent Literature

PTL 1: WO 2016/152659

SUMMARY OF INVENTION

Technical Problem

Since required flowability of a flowable composite resin is different according to practitioners such as dentists, seasons, areas where the resin is used, etc. as described above, a plurality of flowable composite resins of different degrees of flowability have to be offered so as to respond to this.

To respond to this, conventionally, flowability of a flowable composite resin is changed by combining two inorganic particles having largely different particle sizes to change the ratio thereof, and/or by changing the polymerizable monomer and the amount thereof.

Change of the flowability by such a means however deteriorates other properties (such as polishability and abrasion resistance) when the flowability is changed, which is problematic.

With the foregoing problem in view, an object of the present disclosure is to provide a curable dental composite that makes it possible to obtain desired flowability on one hand, and to suppress deterioration of other properties on the other hand.

Solution to Problem

One aspect of the present disclosure is a curable dental composite comprising: a polymerizable monomer; a filler (A); and a filler (B), wherein the filler (A) includes an inorganic particle, and a compound represented by the general formula (1), the compound represented by the general formula (1) covering the inorganic particle, the filler (B) includes another inorganic particle, and a compound represented by the general formula (2), the compound represented by the general formula (2) covering the other inorganic particle, and an average particle size of the filler (B) is 20% to 550% of an average particle size of the filler (A),

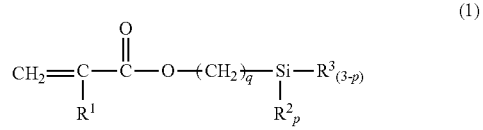

where $R^1$ is a hydrogen atom or a methyl group, $R^2$ is a hydrolysable group, $R^3$ is a $C_{1-6}$ hydrocarbon group, p is 2 or 3, and q is an integer of 6 to 13,

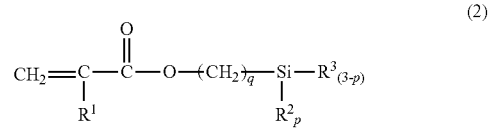

where $R^1$ is a hydrogen atom or a methyl group, $R^2$ is a hydrolysable group, $R^3$ is a $C_{1-6}$ hydrocarbon group, p is 2 or 3, and q is an integer of 1 to 5.

The curable dental composite may be a flowable composite resin.

Advantageous Effects of Invention

The present disclosure may provide a curable dental composite that makes it possible to obtain desired flowability on one hand, and to suppress deterioration of other properties on the other hand.

DESCRIPTION OF EMBODIMENTS

The embodiments for carrying out the present disclosure will be described.

In the present description, the average particle sizes of fillers, inorganic particles, etc. may be obtained by the laser diffraction and scattering method or electron microscope observation.

Results measured by the laser diffraction and scattering method are used for the average particle size of a particle having a particle size of at least 0.10 μm. At this time, measurement is carried out by means of a laser diffraction particle size distribution analyzer (LA-950 manufactured by HORIBA, Ltd.) using a 0.2 mass % sodium hexametaphosphate aqueous solution as a dispersion medium.

In contrast, results measured by electron microscope observation are used for the average particle size of a particle having a particle size smaller than 0.10 μm. At this time, an electron micrograph of 100 fillers is analyzed to obtain a volume average particle size by means of image analysis software WinROOF (manufactured by MITANI CORPORATION), and this obtained size is regarded as the average particle size.

The curable dental composite according to one embodiment of the present disclosure contains a polymerizable monomer, a filler (A), a filler (B) and a filler (C). Hereinafter the constitution of each of them will be described.

<Polymerizable Monomer>

Any polymerizable monomer applied to a dental field can be used for the polymerizable monomer. Among them, a radical polymerizable monomer can be used.

A specific substance of the polymerizable monomer is not particularly limited. Examples thereof include esters of α-cyanoacrylic acid, (meth)acrylic acid, α-haloacrylic acid, crotonic acid, cinnamic acid, sorbic acid, maleic acid, itaconic acid, etc., (meth)acrylamide, (meth)acrylamide derivatives, vinyl esters, vinyl ethers, mono-N-vinyl derivatives and styrene derivatives. Two or more of them may be used in combination. Among them, (meth)acrylic acid esters and (meth)acrylamide derivatives can be used. The polymerizable monomer can be a (meth)acrylic acid ester.

Examples of monofunctional (meth)acrylic acid esters and (meth)acrylamide derivatives include methyl (meth)acrylate, isobutyl (meth)acrylate, benzyl (meth)acrylate, lauryl (meth)acrylate, 2,3-dibromopropyl (meth)acrylate, 2-hydroxyethyl (meth)acrylate, 6-hydroxyhexyl (meth)acrylate, 10-hydroxydecyl (meth)acrylate, propylene glycol mono(meth)acrylate, glycerin mono(meth)acrylate, erythritol mono(meth)acrylate, N-methylol(meth)acrylamide, N-hydroxyethyl(meth)acrylamide, N-(dihydroxyethyl)(meth)acrylamide, (meth)acryloyloxydodecylpyridinium bromide, (meth)acryloyloxydodecylpyridinium chloride, (meth)acryloyloxyhexadecylpyridinium chloride, and (meth)acryloyloxydecylammonium chloride.

Examples of difunctional (meth)acrylic acid esters include ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, 2,2-bis[4-[3-(meth)acryloyloxy-2-hydroxypropoxy]phenyl]propane, 2,2-bis[4-(2-(meth)acryloyloxyethoxy)phenyl]propane, 2,2-bis[4-(meth)acryloyloxypolyethoxyphenyl]propane, 1,2-bis[3-(meth)acryloyloxy-2-hydroxypropoxy]ethane, pentaerythritol di(meth)acrylate, and [2,2,4-trimethylhexamethylene bis(2-carbamoyloxyethyl)]di(meth)acrylate.

Examples of trifunctional or higher (meth)acrylic acid esters include trimethylolpropane tri(meth)acrylate, trimethylolethane tri(meth)acrylate, tetramethylolmethane tri(meth)acrylate, pentaerythritol tetra(meth)acrylate, dipentaerythritol hexa(meth)acrylate, N,N'-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane.

The polymerizable monomer is such that the refractive index of the polymer after polymerization thereof can be 1.52 to 1.58 and further may be 1.53 to 1.58. This may lead to an excellent match intraorally, to improve esthetics.

Here, the refractive index means a refractive index measured at 25° C. by means of an Abbe refractometer.

The polymerizable monomer can be such that the mass ratio thereof to the total mass of the filler (A), the filler (B) and filler (C) is 0.1 to 1.5, which may be 0.25 to 0.65. This may improve handleability of the curable dental composite.

<Filler (A)>

An inorganic particle ($A_0$) is surface-treated so as to be covered to form a particle, which is the filler (A).

The inorganic particle ($A_0$) is not particularly limited. Examples thereof include various glasses whose main component is silica and which contain an oxide of a heavy metal, boron, aluminum or the like as necessary (such as E-glass, barium glass, and lanthanum glass ceramics), various ceramics, composite oxides (such as silica-titania composite oxide and silica-zirconia composite oxide), kaolin, clay minerals (such as montmorillonite), mica, ytterbium fluoride, and yttrium fluoride. Two or more of them may be used in combination.

Examples of commercially available products of such an inorganic particle ($A_0$) include GO18-053, GM27884, 8235, and GM31684 (manufactured by Schott AG), and E2000 and E3000 (manufactured by ESSTECH Inc.).

The filler (A) is formed by surface treatment such that the inorganic particle ($A_0$) is covered with a compound represented by the following general formula (1).

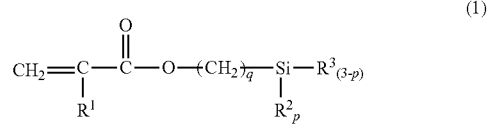

(1)

$R^1$ in the general formula (1) is a hydrogen atom or a methyl group.

$R^2$ in the general formula (1) is a particularly unlimited hydrolysable group. Examples thereof include alkoxy groups such as a methoxy group, an ethoxy group and a butoxy group, a chlorine atom, and an isocyanate group.

$R^3$ in the general formula (1) is a particularly unlimited $C_{1-6}$ hydrocarbon group. Examples thereof include $C_{1-6}$ alkyl groups, $C_{2-6}$ alkenyl groups, and $C_{2-6}$ alkynyl groups.

$C_{1-6}$ alkyl groups may be either linear, branched, or cyclic. Examples thereof include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, a cyclopropyl group, a cyclobutyl group, a cyclopentyl group, and a cyclohexyl group.

$C_{2-6}$ alkenyl groups may be either linear, branched, or cyclic. Examples thereof include a vinyl group, an allyl group, a methylvinyl group, a butenyl group, a pentynyl group, a hexynyl group, a cyclopropenyl group, a cyclobutenyl group, a cyclopentynyl group, and a cyclohexynyl group.

$C_{2-6}$ alkynyl groups may be either linear, branched, or cyclic. Examples thereof include an ethynyl group, a 1-propynyl group, a 2-propynyl group, a 1-butynyl group, a 1-methyl-2-propynyl group, a 2-butynyl group, a 3-butynyl group, a 1-pentynyl group, a 1-ethyl-2-propynyl group, a 2-pentynyl group, a 3-pentynyl group, a 1-methyl-2-butynyl group, a 4-pentynyl group, a 1-methyl-3-butynyl group, a 2-methyl-3-butynyl group, a 1-hexynyl group, a 2-hexynyl group, a 1-ethyl-2-butynyl group, a 3-hexynyl group, a 1-methyl-2-pentynyl group, a 1-methyl-3-pentynyl group, a 4-methyl-1-pentynyl group, a 3-methyl-1-pentynyl group, a 5-hexynyl group, and a 1-ethyl-3-butynyl group.

p in the general formula (1) is 2 or 3.

q in the general formula (1) is an integer of 6 to 13, which can be 8 to 13.

The compound represented by the general formula (1) is not particularly limited. Examples thereof include 6-methacryloyloxyhexyltrimethoxysilane, 7-methacryloyloxyheptyltrimethoxysilane, 8-methacryloyloxyoctyltrimethoxysilane, 8-acryloyloxyoctyltrimethoxysilane, 8-methacryloyloxyoctyltriethoxysilane, 9-methacryloyloxynonyltrimethoxysilane, 10-methacryloyloxydecyltrimethoxysilane, 11-methacryloyloxyundecyltrimethoxysilane, 11-methacryloyloxyundecyldichloromethylsilane, 11-methacryloyloxyundecyltrichlorosilane, 11-methacryloyloxyundecyldimethoxymethylsilane, 12-methacryloyloxydodecyltrimethoxysilane, and 13-methacryloyloxytridecyltrimethoxysilane. Two or more of them may be used in combination. Among them, the compound can be 8-methacryloyloxyoctyltrimethoxysilane, 9-methacryloyloxynonyltrimethoxysilane, 10-methacryloyloxydecyltrimethoxysilane, or 11-methacryloyloxyundecyltrimethoxysilane.

The way of the surface treatment in the filler (A) is not particularly limited. Examples thereof include the ways of: spraying a solution such that the compound represented by the general formula (1) is diluted in a solvent over the inorganic particle ($A_0$) as stirring the inorganic particle ($A_0$) in a mixing tank, to heat and dry the sprayed and stirring inorganic particle in the tank for a certain time; and stirring and mixing the inorganic particle ($A_0$) and the compound represented by the general formula (1) in a solvent, and thereafter heating and drying the mixture.

The mass ratio of the compound represented by the general formula (1) to the inorganic particle ($A_0$) can be 0.005 to 0.15, and may be 0.01 to 0.13.

The average particle size of the filler (A) may be 0.1 μm to 0.9 m, and can be 0.15 μm to 0.7 μm. The average particle size of the filler (A) less than 0.1 μm may lower the flexural strength of the curable dental composite, and the average particle size of the filler (A) more than 0.9 μm may lower the flexural strength, abrasion resistance, and polishability of the curable dental composite.

The filler (A) may be spherical, and can be amorphous, which enlarges the specific surface area of the filler (A). This leads to strong bonding with the polymerizable monomer, which may improve the flexural strength.

The refractive index of the filler (A) may be 1.52 to 1.58, and can be 1.53 to 1.58. The difference between the refractive index of the polymer from the polymerizable monomer, and that of the filler (A) can be at most 0.03.

The filler (A) has only to be contained in the curable dental composite of the present embodiment, and the amount thereof is suitably adjusted as necessary.

<Filler (B)>

An inorganic particle ($B_0$) is surface-treated so as to be covered to form a particle, which is the filler (B).

The same as the inorganic particle ($A_0$) may be used as the inorganic particle ($B_0$).

The filler (B) is formed by surface treatment such that the inorganic particle ($B_0$) is covered with a compound represented by the following general formula (2).

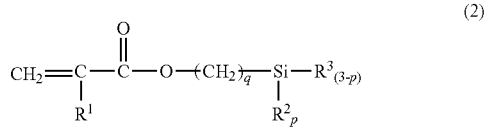

(2)

In the compound represented by the general formula (2), q is an integer of 1 to 5. $R^1$, $R^2$ and p, other than q, may be regarded the same as in the compound represented by the general formula (1), q in the general formula (2) can be an integer of 1 to 3.

The compound represented by the general formula (2) is not particularly limited. Examples thereof include 3-methacryloyloxypropyltrimethoxysilane, 3-acryloyloxypropyltrimethoxysilane, 3-methacyloyloxypropyltriethoxysilane, 3-methacryloyloxypropyldimethoxysilane, and 4-methacryloyloxybutyltrimethoxysilane. Two or more of them may be used in combination. Among them, the compound can be 3-methacryloyloxypropyltrimethoxysilane.

The mass ratio of the compound represented by the general formula (2) to the inorganic particle ($B_0$) may be 0.005 to 0.15, and can be 0.01 to 0.13. Refractive indexes concerning, and the shape of the filler (B) may be also regarded the same as in the filler (A).

The average particle size of the filler (B) may be such that the difference thereof from that of the filler (A) is held down within a predetermined range. Specifically, the average particle size of the filler (B) contained in the curable dental composite is 20% to 550% of that of the filler (A), where the average particle size of the filler (A) may be made to be closer to that of the filler (B). This may suppress undesired deterioration of properties which is caused by the difference between two fillers in particle size, and may offer a wider control range of the flowability as each property is satisfied. In such a view, the average particle size of the filler (B) contained in the curable dental composite can be 25% to 400% of that of the filler (A), and may be 50% to 250% thereof.

The filler (B) has only to be contained in the curable dental composite of the present embodiment, and the amount thereof is suitably adjusted as necessary.

<Relationship Between Filler (A) and Filler (B)>

Just changing the mixing ratio of the filler (A) and the filler (B) in the curable dental composite may change the flowability of the curable dental composite.

Here, in the curable dental composite of the present embodiment, the difference between the filler (A) and the filler (B) in average particle size is within a predetermined range as described above. This does not necessitate coexistence of two fillers having largely different particle sizes for adjusting the flowability, which may suppress deterioration of properties which is caused by such coexistence of fillers having largely different particle sizes.

The material and the particle size of the inorganic particle ($A_0$) may be the same as those of the inorganic particle ($B_0$). This is an advantage even in the cost since the same material is used.

As is seen from the general formulae (1) and (2), the structures of the compounds with which the filler (A) and the filler (B) are covered are very similar, and thus properties thereof are also highly similar, which may suppress change in properties other than the flowability. This can suppress deterioration of the other properties, and can only change the flowability.

The mass ratio of the filler (A) to the total mass of the filler (A) and the filler (B)(the total mass of the fillers), and the mass ratio of the filler (B) to the total mass of the fillers may be changed according to required flowability. A high mass ratio of the filler (A) to the total mass of the fillers leads to low flowability, and a high mass ratio of the filler (B) to the total mass of the fillers leads to high flowability.

As the above, according to the present embodiment, changing the mixing ratio of the filler (A) and the filler (B)

may change the flowability of the curable dental composite. As described above, the flowability can be adjusted without other properties (polishability and abrasion resistance) lowered even if being changed.

Here, "flowability" may be quantified and compared by measuring "sagging" and "strength of extrusion". Measurement of "sagging" and "strength of extrusion" will be described later.

<Filler (C)>

The filler (C) has only to have a feature of at least one of the following three aspects. Therefore, the filler (C) may have any one of the following three aspects, or an aspect including some of these three.

This filler (C) may suppress liquid separation of the curable dental composite.

A first aspect of the filler (C) is a particle on the surface of which a group represented by the general formula (3) is present.

In the general formula (3). $R^4$ and R are each independently a methyl group or an ethyl group.

A second aspect of the filler (C) is a particle on the surface of which a group represented by the general formula (4) is present.

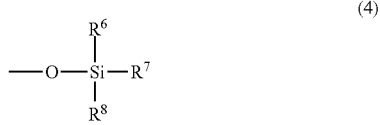

In the general formula (4), $R^6$, $R^7$ and $R^8$ are each independently a methyl group or an ethyl group.

An inorganic particle ($C_0$) is surface-treated so as to be covered to form a particle, which is a third aspect of the filler (C).

The inorganic particle ($C_0$) is not particularly limited. Examples thereof include inorganic oxides such as silica, alumina, titania, and zirconia, and composite oxides thereof, calcium phosphate, hydroxyapatite, yttrium fluoride, ytterbium fluoride, barium titanate, and potassium titanate. Among them, silica, alumina, titania, silica-alumina composite oxide, and silica-zirconia composite oxide are preferable.

Examples of commercially available products of such an inorganic particle ($C_0$) include AEROSIL 200, and OX-50 (both manufactured by NIPPON AEROSIL CO., LTD.).

The filler (C) of this aspect is formed by surface treatment such that the inorganic particle ($C_0$) is covered with a compound represented by the following general formula (5).

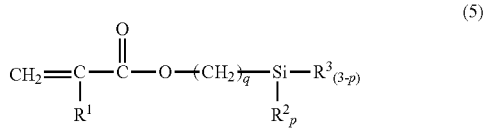

In the general formula (5), $R^1$ is a hydrogen atom or a methyl group, $R^2$ is a hydrolysable group. $R^3$ is a $C_{1-6}$ hydrocarbon group, p is 2 or 3, and q is an integer of 1 to 6.

The compound represented by the general formula (5) is not particularly limited. Examples thereof include 3-methacryloyloxypropyltrimethoxysilane, 3-acryloyloxypropyltrimethoxysilane, 3-methacryloyloxypropyltriethoxysilane, 3-methacryloyloxypropyldimethoxysilane, and 4-methacryloyloxybutyltrimethoxysilane. Two or more of them may be used in combination. Among them, the compound may be 3-methacryloyloxypropyltrimethoxysilane.

The way of making the filler (C) is not particularly limited. Examples thereof include: surface-treating the particle with a silane coupling agent in the cases of the first and second aspects; and surface-treating the inorganic particle ($C_0$) with the compound represented by the general formula (5) in the case of the third aspect.

Here, the silane coupling agent is not specifically restricted as long as the group represented by the general formula (3), and/or the group represented by the general formula (4) may be introduced on the surface of the particle. Examples thereof include dimethyldichlorosilane and hexamethyldisilazane.

More specific examples of the way of making the filler (C) include the ways of: spraying a solution such that the silane coupling agent (first and second aspects) or the compound represented by the general formula (5) is diluted in a solvent over a base particle as stirring the base particle in a mixing tank, to heat and dry the sprayed and stirring particle in the tank for a certain time; and stirring and mixing a base particle, and the silane coupling agent or the compound represented by the general formula (5) in a solvent, and thereafter heating and drying the mixture.

The average particle size of the filler (C) is at least 5 nm and less than 50 nm, and can beat least 5 nm and less than 20 nm. The average particle size of the filler (C) less than 5 nm leads to difficulty in production.

The filler (C) may be spherical, and may be amorphous. The filler (C) may be a primary particle that does not agglomerate, and may be a secondary particle of agglomerating primary particles.

The refractive index of the filler (C) can be 1.43 to 1.50, which may be 1.43 to 1.46. The difference between the refractive index of the polymer from the polymerizable monomer, and that of the filler (C) can be at least 0.05.

Examples of commercially available products of the filler (C) include AEROSIL R812, R972, and RX-50 (all manufactured by NIPPON AEROSIL CO., LTD.).

The mass ratio of the filler (C) to the total mass of the filler (A), the filler (B), and the filler (C) can be 0.001 to 0.015, which may be 0.001 to 0.010. This mass ratio lower than 0.001 easily causes liquid separation of the curable dental composite, and the mass ratio higher than 0.015 tends to lead to a more cobwebbing curable dental composite.

<Polymerization Initiator>

The curable dental composite may further contain a polymerization initiator. When the curable dental composite is cured at ambient temperature, a redox polymerization initiator may be used.

The redox polymerization initiator is not particularly limited. Examples thereof include organic peroxide/amine-based, and organic peroxide/amine/sulfinic acid (or a salt thereof)-based redox polymerization initiators. When the redox polymerization initiator is used, an aspect of packaging thereof has to be such that an oxidizing agent and a reducing agent are separately packed, and both have to be mixed just before use.

The oxidizing agent is not particularly limited. Examples thereof include organic peroxides such as diacyl peroxides, peroxyesters, peroxycarbonates, dialkyl peroxides, peroxyketals, ketone peroxides, and hydroperoxides.

Examples of diacyl peroxides include benzoyl peroxide, 2,4-dichlorobenzoyl peroxide, m-toluoyl peroxide, and lauroyl peroxide.

Examples of peroxyesters include t-butyl peroxybenzoate, di-t-butyl peroxyisophthalate, and t-butyl peroxy-2-ethylhexanoate.

Examples of peroxycarbonates include t-butyl peroxy isopropyl carbonate.

Examples of dialkyl peroxides include dicumyl peroxide, di-t-butyl peroxide, and 2,5-dimethyl-2,5-bis(benzoylperoxy)hexane.

Examples of peroxyketals include 1,1-bis(t-butylperoxy)-3,3,5-trimethylcyclohexane.

Examples of ketone peroxides include methyl ethyl ketone peroxide.

Examples of hydroperoxides include t-butyl hydroperoxide.

The reducing agent is not particularly limited. Examples thereof include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-isopropylaniline. N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, ethyl 4-dimethylaminobenzoate, n-butoxyethyl 4-dimethylaminobenzoate, 2-methacryloyloxyethyl 4-dimethylaminobenzoate, trimethylamine, triethylamine, N-methyldiethanolamine, N-ethyldiethanolamine, N-n-butyldiethanolamine, N-lauryldiethanolamine, triethanolamine. (2-dimethylamino)ethyl methacrylate. N-methyldiethanolamine dimethacrylate, N-ethyldiethanolamine dimethacrylate, triethanolamine monomethacrylate, triethanolanine dimethacrylate, and triethanolamine trimethacrylate.

As a redox polymerization initiator other than the foregoing, tributylborane, organic sulfinic acid, or the like may be used, in addition to a cumene hydroperoxide/thiourea-based, an ascorbic acid/$Cu^{2+}$ salt-based, or an organic sulfinic acid (or a salt thereof)/amine/inorganic peroxide-based redox initiator.

When the curable dental composite is irradiated with visible radiation to be cured, a photopolymerization initiator may be used. The photopolymerization initiator is not particularly limited. Examples thereof include redox initiators such as α-diketone/reducing agent, ketal/reducing agent, and thioxanthone/reducing agent.

Examples of α-diketones include camphorquinone, benzil, and 2,3-pentanedione.

Examples of ketals include benzyl dimethylketal, and benzyl diethyl ketal.

Examples of thioxanthone include 2-chlorothioxanthone, and 2,4-diethylthioxanthone.

Examples of the reducing agents include tertiary amines such as Michler's ketone, 2-(dimethylamino)ethyl methacrylate, N,N-bis[(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylamino benzophenone, N,N-bis(2-hydroxyethyl)-p-toluidine, and dimethylamino phenanthrol; aldehydes such as citronellal, lauryl aldehyde, phthaldialdehyde, dimethylamino benzaldehyde, and terephthalaldehyde; and compounds having a thiol group such as 2-mercaptobenzoxazole, decanethiol, 3-mercaptopropyltrimethoxysilane, 4-mercaptoacetophenone, thiosalicylic acid, and thiobenzoic acid.

An organic peroxide may be added to the redox initiator.

When the curable dental composite is irradiated with ultraviolet radiation to be cured, a photopolymerization initiator may be used. The photopolymerization initiator is not particularly limited. Examples thereof include benzoin alkyl ethers, benzyl dimethyl ketals, acylphosphine oxides, and bisacylphosphine oxides.

Examples of acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl bis(2,6-dimethylphenyl)phosphonate, and 2,4,6-trimethylbenzoylethoxyphenylphosphine oxide.

Examples of bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, and bis(2,4,6-trimethylbenzoyl)phenylphosphine oxide.

A water-soluble substituent may be substituted in a (bis) acylphosphine oxide.

(Bis)acyl phosphine oxides may be used in combination with reducing agents such as amines, aldehydes, mercaptans, and sulfinic acid salts.

The mass ratio of the polymerization initiator to the polymerizable monomer can be 0.001 to 0.1, which may be 0.002 to 0.05.

<Other Contents>

The curable dental composite may further contain a polymerization inhibitor, a UV absorber, a fluorescent agent, and a pigment.

The polymerization inhibitor is not particularly limited. Examples thereof include 3,5-dibutyl-4-hydroxytoluene, hydroquinone, dibutylhydroquinone, dibutylhydroquinone monomethyl ether, 2,6-t-butylphenol, and 4-methoxyphenol. Two or more of them may be used in combination.

<Aspect of Curable Dental Composite>

The curable dental composite may be a paste of dispersing the filler (A) and the filler (B) in the polymerizable monomer, and may be a molded body of dispersing the filler (A) and the filler (B) in the polymer from the polymerizable monomer.

For example, an intraoral cavity may be directly filled with a pasty curable dental composite of dispersing the filler (A) and the filler (B) in the polymerizable monomer, to be given treatment. After a paste of dispersing the filler (A) and the filler (B) in the polymerizable monomer is extraorally cured to be molded, the molded body may be intraorally attached using a dental adhesive.

Here, when the curable dental composite is chemically polymerizable, or when the curable dental composite is chemically polymerizable and photopolymerizable, such a mode may be adopted that an aspect of packaging is such that a composition containing the oxidizing agent and a composition containing the reducing agent are separately packed, and both are mixed just before the curable dental composite is used.

The curable dental composite may be a flowable composite resin. At that time, the flowable composite resin may be one agent, and may be two agents.

Strength for extruding the flowable composite resin can be usually at most kgf. This may improve the formability and handleability of the flowable composite resin.

For example, the flowable composite resin is offered as a package having a syringe filled with the flowable composite resin, a plunger that is fitted to the syringe from the rear end of the syringe, and a needle chip that is to be attached to the tip of the syringe.

The inner diameter of a needle that the needle chip has may be 0.3 mm to 0.9 mm.

For example, a package of a two-agent flowable composite resin may have parallelly linked two syringes and parallelly linked two plungers, and a static mixer may be provided for the tips of both syringes.

<Producing Method>

For example, the curable dental composite as described above may be produced as follows without any specific limitation:

an original liquid of solving and admixing the foregoing polymerizable monomer, and a catalyst is prepared; and the filler (A), the filler (B), the filler (C), which are made as the above description, the original liquid, and necessary materials such as a pigment are loaded and kneaded by means of a mixer, to form the curable dental composite.

The stage of a precursor by a combination of a part of the foregoing materials, or pretreatment may be included in the middle of the production steps for improving production efficiency. Setting the order, division of the loading amount, etc. may be suitably carried out for improving kneading efficiency.

EXAMPLES

Examples will be described hereinafter. The present invention is not limited to these examples.

<Preparation of Materials>

[Filler ($A_1$)]

An amorphous barium glass particle having an average particle size of 0.18 μm, GM27884 NanoFine 180 (manufactured by Schott AG) was surface-treated with 8-methacryloyloxyoctyltrimethoxysilane, and then the filler ($A_1$) having an average particle size of 0.18 μm was obtained as a filler ($A_1$) that was a kind of the filler (A).

[Filler ($A_2$)]

A barium glass particle having an average particle size of 0.40 μm, GM27884 UltraFine 0.4 (manufactured by Schott AG) was surface-treated with 8-methacryloyloxyoctyltrimethoxysilane, and then the filler ($A_2$) having an average particle size of 0.40 μm was obtained as a filler ($A_2$) that was a kind of the filler (A).

[Filler ($A_3$)]

A barium glass particle having an average particle size of 0.70 μm, GM27884 UltraFine 0.7 (manufactured by Schott AG) was surface-treated with 8-methacryloyloxyoctyltrimethoxysilane, and then the filler ($A_3$) having an average particle size of 0.70 μm was obtained as a filler ($A_3$) that was a kind of the filler (A).

[Filler ($A_4$)]

A barium glass particle having an average particle size of 1.0 μm, GM27884 UltraFine 2.0 (manufactured by Schott AG) was surface-treated with 8-methacryloyloxyoctyltrimethoxysilane, and then the filler ($A_4$) having an average particle size of 1.0 μm was obtained as a filler ($A_4$) that was a kind of the filler (A).

[Filler ($B_1$)]

As a filler ($B_1$) that was a kind of the filler (B), the filler ($B_1$) having an average particle size of 0.18 μm was obtained in the same manner as the filler ($A_1$) except that 3-methacryloyloxypropyltrimethoxysilane was used instead of 8-methacryloyloxyoctyltrimethoxysilane as the material for the surface treatment.

[Filler ($B_2$)]

As a filler ($B_2$) that was a kind of the filler (B), the filler ($B_2$) having an average particle size of 0.4 μm was obtained in the same manner as the filler ($A_2$) except that 3-methacryloyloxypropyltrimethoxysilane was used instead of 8-methacryloyloxyoctyltrimethoxysilane as the material for the surface treatment.

[Filler ($B_3$)]

As a filler ($B_3$) that was a kind of the filler (B), the filler ($B_3$) having an average particle size of 0.7 μm was obtained in the same manner as the filler ($A_3$) except that 3-methacryloyloxypropyltrimethoxysilane was used instead of 8-methacryloyloxvoctyltrimethoxysilane as the material for the surface treatment.

[Filler ($B_4$)]

As a filler ($B_4$) that was a kind of the filler (B), the filler ($B_4$) having an average particle size of 1.0 μm was obtained in the same manner as the filler ($A_4$) except that 3-methacryloyloxypropyltrimethoxysilane was used instead of 8-methacryloyloxyoctyltrimethoxysilane as the material for the surface treatment.

Table 1 summarizes the prepared filler ($A_1$) to filler ($A_4$) and filler ($B_1$) to filler ($B_4$).

TABLE 1

| Filler | Average particle size (μm) | Material for surface treatment |
|---|---|---|
| $A_1$ | 0.18 | 8-methacryloyloxyoctyltrimethoxysilane |
| $A_2$ | 0.40 | 8-methacryloyloxyoctyltrimethoxysilane |
| $A_3$ | 0.70 | 8-methacryloyloxyoctyltrimethoxysilane |
| $A_4$ | 1.0 | 8-methacryloyloxyoctyltrimethoxysilane |
| $B_1$ | 0.18 | 3-methacryloyloxypropyltrimethoxysilane |
| $B_2$ | 0.40 | 3-methacryloyloxypropyltrimethoxysilane |
| $B_3$ | 0.70 | 3-methacryloyloxypropyltrimethoxysilane |
| $B_4$ | 1.0 | 3-methacryloyloxypropyltrimethoxysilane |

[Filler ($C_1$)]

As a filler ($C_1$) that was the filler (C), AEROSIL R812 (manufactured by NIPPON AEROSIL CO., LTD.), which is a silica particle surface-treated with hexamethyldisilazane, having an average particle size of 7 nm, was prepared.

[Polymerizable Monomer Composite]

A mixture of polymerizable monomers was obtained by mixing 30 parts by mass of di-2-methacryloyloxyethyl-2,2,4-trimethylhexamethylene dicarbamate (UDMA), 50 parts by mass of 2,2-bis[4-(2-methacryloyloxyethoxy)phenyl]propane (Bis-MEPP), 10 parts by mass of triethylene glycol dimethacrylate (3G), and 10 parts by mass of trimethylolpropane trimethacrylate (TMPT).

To this mixture of polymerizable monomers, 1 part by mass of camphorquinone (CQ), 2 parts by mass of ethyl 4-dimethylaminobenzoate, 0.2 parts by mass of diethyl-2,5-dihydroxyterephthalate (LZ), and 0.2 parts by mass of 2,5-bis(5'-t-butylbenzoxazolyl-2')thiophene (TF) were each added, to obtain a polymerizable monomer composite.

<Curable Dental Composite>

Example 1

To 50 parts by mass of the polymerizable monomer composite, 1 part by mass of the filler ($A_1$), 99 parts by mass of the filler ($B_1$), and 0.5 parts by mass of the filler ($C_1$) were added, mixed and kneaded to be uniform, and thereafter defoamed in a vacuum, to obtain a pasty curable dental composite (flowable composite resin) according to Example 1.

Example 2

A pasty curable dental composite (flowable composite resin) according to Example 2 was obtained in the same manner as in Example 1 except that 1 part by mass of the filler ($A_1$) and 99 parts by mass of the filler ($B_1$) in Example 1 were changed to 25 parts by mass of the filler ($A_1$) and 75 parts by mass of the filler ($B_1$).

Example 3

A pasty curable dental composite (flowable composite resin) according to Example 3 was obtained in the same manner as in Example 1 except that 1 part by mass of the filler ($A_1$) and 99 parts by mass of the filler ($B_1$) in Example 1 were changed to 99 parts by mass of the filler ($A_1$) and 1 part by mass of the filler ($B_1$).

Example 4

A pasty curable dental composite (flowable composite resin) according to Example 4 was obtained in the same manner as in Example 2 except that 75 parts by mass of the filler ($B_1$) in Example 2 were changed to 75 parts by mass of the filler ($B_2$).

Example 5

A pasty curable dental composite (flowable composite resin) according to Example 5 was obtained in the same manner as in Example 2 except that 75 parts by mass of the filler ($B_1$) in Example 2 were changed to 75 parts by mass of the filler ($B_3$).

Example 6

A pasty curable dental composite (flowable composite resin) according to Example 6 was obtained in the same manner as in Example 2 except that 25 parts by mass of the filler ($A_1$) in Example 2 were changed to 25 parts by mass of the filler ($A_2$).

Example 7

A pasty curable dental composite (flowable composite resin) according to Example 7 was obtained in the same manner as in Example 2 except that 25 parts by mass of the filler ($A_1$) in Example 2 were changed to 25 parts by mass of the filler ($A_3$).

Comparative Example 1

A pasty curable dental composite (flowable composite resin) according to Comparative Example 1 was obtained in the same manner as in Example 2 except that 75 parts by mass of the filler ($B_1$) in Example 2 were changed to 75 parts by mass of the filler ($B_4$).

Comparative Example 2

A pasty curable dental composite (flowable composite resin) according to Comparative Example 2 was obtained in the same manner as in Example 2 except that parts by mass of the filler ($A_1$) in Example 2 were changed to 25 parts by mass of the filler ($A_4$).

Table 2 summarizes the features of Examples 1 to 7 and Comparative Examples 1 and 2. In Table 2, "Proportion of particle size" indicates the proportion of the average particle size of the filler (B) to that of the filler (A), which is a value calculated by dividing the average particle size of the filler (B) by that of the filler (A), and multiplying the result by 100(%).

TABLE 2

| | Filler (A) | | | Filler (B) | | | Polymerizable |
|---|---|---|---|---|---|---|---|
| | Kind | Av. particle size (μm) | Loading amount (parts by mass) | Kind | Av. particle size (μm) | Loading amount (parts by mass) | Proportion of particle size (%) | monomer Loading amount (parts by mass) |
| Ex. 1 | $A_1$ | 0.18 | 1 | $B_1$ | 0.18 | 99 | 100 | 50 |
| Ex. 2 | $A_1$ | 0.18 | 25 | $B_1$ | 0.18 | 75 | 100 | 50 |
| Ex. 3 | $A_1$ | 0.18 | 99 | $B_1$ | 0.18 | 1 | 100 | 50 |
| Ex. 4 | $A_1$ | 0.18 | 25 | $B_2$ | 0.40 | 75 | 222 | 50 |
| Ex. 5 | $A_1$ | 0.18 | 25 | $B_3$ | 0.70 | 75 | 389 | 50 |
| Ex. 6 | $A_2$ | 0.40 | 25 | $B_1$ | 0.18 | 75 | 45 | 50 |
| Ex. 7 | $A_3$ | 0.70 | 25 | $B_1$ | 0.18 | 75 | 26 | 50 |
| Comp. Ex. 1 | $A_1$ | 0.18 | 25 | $B_4$ | 1.0 | 75 | 556 | 50 |
| Comp. Ex. 2 | $A_4$ | 1.0 | 25 | $B_1$ | 0.18 | 75 | 18 | 50 |

<Evaluation>

Each of the foregoing examples and comparative examples was variously evaluated by using a cylindrical plunger that was fitted into a syringe from the rear end of the syringe, and a needle chip (20G) that was to be attached to the tip of the syringe, after the cylindrical syringe made from a polyolefin resin (tube for Unifil Flow, inner diameter: 6.3 mm, length: 63.0 mm) was filled with the made curable dental composite. Here, a needle that the needle chip had was 0.65 mm in inner diameter and 13 mm in length, and bended at a position 7.5 mm away from the tip at 50°. The syringe and the plunger were made from ambient light-non-transmissive materials. Hereinafter specific evaluation items will be described.

[Sagging]

Sagging was evaluated as one index indicating flowability, and was measured specifically as follows:

the foregoing syringe was filled with 1.0 mL of the quantity of the curable dental composite, thereafter the needle chip was attached to the tip of the syringe, and the plunger was pushed to extrude 0.1 g of the quantity of the curable dental composite from the tip of the needle chip; after 30 seconds had passed since the discharge, fixation by a jig or the like was carried out so that the curable dental composite was perpendicular, and the full length of the composite having run down after 1 minute had passed was measured to be applied to sagging.

[Strength of Extrusion]

Strength of extrusion was evaluated as another index indicating flowability, and was measured specifically as follows:

the foregoing syringe was filled with 1.0 mL of the quantity of the curable dental composite, thereafter the needle chip was attached to the tip of the syringe, and the plunger was pushed to extrude the curable dental composite from the tip of the needle chip; at this time, strength of extrusion was measured using a universal testing machine AG-IS (manufactured by SHIMADZU CORPORATION) at 25° C.; specifically, a crosshead to which a jig for the compressive strength test was attached was descended at 10 mm/min as holding a containment vessel in the vertical direction, and the curable dental composite was extruded as a load was applied thereto; the maximum load at that time was applied to strength of extrusion.

[Abrasion Resistance]

After a dedicated metal mold was filled with the curable dental composite, the top and the bottom were subjected to pressure contact with slide glass. Next, both top and bottom faces were irradiated with visible radiation for 10 seconds using G-Light Prima II (manufactured by GC Corporation) to cure the curable dental composite. Further, after taken out of the metal mold, the cured composite was kept in distilled water at 37° C. for 24 hours, to obtain a test piece. Each test piece was attached to an occlusion abrasion tester (manufactured by Tokyo Giken, Inc.), and after an unpolymerized layer was polished with #1000 abrasive paper, the full length of the test piece before test was measured. A slurry of kneading glycerin and ACRYCON AC (manufactured by MITSUBISHI RAYON CO., LTD.) of equal amounts was spread in the occlusion abrasion tester, the test assuming 100.000 vertical and lateral occlusions against a PMMA plate was performed. After the test, the full length of each test piece was measured, and the difference between before and after the test was defined as an abrasion loss, to evaluate abrasion resistance. The case where the abrasion loss was at most 10 μm got a pass.

[Polishability]

After a metal mold of 15 mm in diameter and 1.5 mm in thickness was filled with the curable dental composite, the top and the bottom were subjected to pressure contact with slide glass. Next, nine points at each of both top and bottom faces were irradiated with visible radiation for 10 seconds per point using G-Light Prima II (manufactured by GC Corporation) to cure the curable dental composite. Further, the cured composite was taken out of the metal mold, to obtain a test piece. Next, a smooth face of the test piece was polished using #600 abrasive paper under a drying condition. Further, by means of MICROMOTOR LM-III (manufactured by GC Corporation) under a water pouring condition, polishing was carried out at approximately 10000 rpm in rotational speed for 10 seconds using PRE SHINE (manufactured by GC Corporation), and thereafter polishing was carried out at approximately 10000 rpm in rotational speed for 10 seconds using DIA SHINE (manufactured by GC Corporation). Further, the gloss of the polished face was measured at 60° in measurement angle using Gloss Meter VG-2000 (manufactured by NIPPON DENSHOKU INDUSTRIES CO., LTD.). Polishability was evaluated by the degree of the gloss which was the proportion of the gloss of the polished face to that of a mirror, which was defined as 100. The case where the degree of the gloss was at least 60% got a pass.

[Results]

Table 3 shows the evaluation results. In Table 3, the range of required values in each Example is also shown for sagging and strength of extrusion.

TABLE 3

| | Sagging (mm) | | Strength of extrusion (kgf) | | Abrasion loss (μm) | Degree of gloss (%) |
| --- | --- | --- | --- | --- | --- | --- |
| | Measured value | Desired range | Measured value | Desired range | | |
| Ex. 1 | 28.1 | 25-35 | 7 | at most 8 | 5 | 66 |
| Ex. 2 | 8.2 | 6-10 | 4 | at most 5 | 4 | 70 |
| Ex. 3 | 5.1 | 4-6 | 2 | at most 5 | 3 | 71 |
| Ex. 4 | 9.6 | 8-12 | 3 | at most 5 | 5 | 67 |
| Ex. 5 | 10.6 | 9-13 | 3 | at most 5 | 7 | 62 |
| Ex. 6 | 9.0 | 8-12 | 3 | at most 5 | 4 | 68 |
| Ex. 7 | 9.9 | 9-13 | 3 | at most 5 | 6 | 63 |
| Comp. Ex. 1 | 12.7 | 10-14 | 3 | at most 5 | 25 | 44 |
| Comp. Ex. 2 | 10.9 | 10-14 | 4 | at most 5 | 21 | 49 |

As seen from Examples 1 to 7 in Table 3, the proportions of the average particle sizes of the filler (A) and the filler (B) within predetermined ranges may make flowability including sagging and strength of extrusion within a desired range on one hand, and make it possible to obtain necessary performance on abrasion resistance and polishability that are other properties on the other hand.

In contrast, as seen from Comparative Examples 1 and 2 in Table 3, the proportions of the average particle sizes of the filler (A) and the filler (B) outside predetermined ranges lead to unsatisfied performance of at least one of abrasion resistance (abrasion loss) and polishability (degree of gloss) when flowability including sagging and strength of extrusion is within a desired range. In the present Examples, both abrasion resistance and polishability result in unsatisfied performance.

Among Examples 1 to 7, Examples 1 to 3, next Examples 4 and 6, and then Examples 5 and 7 in order of merit might have a wide adjustable range of flowability as each performance was satisfied. With such in view, it was found that the proportion of the average particle size of approximately 100% more notably gives an effect.

The invention claimed is:

1. A curable dental composite comprising:
    a polymerizable monomer;
    a filler (A) having an average particle size of 0.18 μm to 0.7 μm, and
    a filler (B) having an average particle size of 0.18 μm to 0.7 μm,
    wherein the filler (A) includes an inorganic particle, and a compound represented by the general formula (1), the compound represented by the general formula (1) covering the inorganic particle,
    the filler (B) includes another inorganic particle, and a compound represented by the general formula (2), the compound represented by the general formula (2) covering the other inorganic particle, and
    the average particle size of the filler (B) is 45% to 222% of the average particle size of the filler (A),

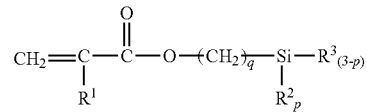
(1)

where $R^1$ is a hydrogen atom or a methyl group, $R^2$ is a hydrolysable group, $R^3$ is a $C_{1-6}$ hydrocarbon group, p is 2 or 3, and q is an integer of 6 to 13,

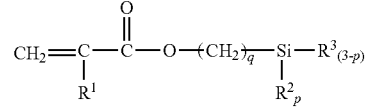
(2)

where $R^1$ is a hydrogen atom or a methyl group, $R^2$ is a hydrolysable group, $R^3$ is a $C_{1-6}$ hydrocarbon group, p is 2 or 3, and q is an integer of 1 to 5.

2. The curable dental composite according to claim 1, wherein the curable dental composite is a flowable composite resin.

* * * * *